United States Patent
Janzen et al.

(10) Patent No.: US 11,690,384 B2
(45) Date of Patent: Jul. 4, 2023

(54) STREPTOCOCCUS THERMOPHTLUS (ST) CELL TO MAKE E.G. MOZZARELLA CHEESE

(71) Applicant: Chr. Hansen A/S, Hoersholm (DK)

(72) Inventors: Thomas Janzen, Hoersholm (DK); Ditte Ellegaard Christiansen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 145 days.

(21) Appl. No.: 16/642,787

(22) PCT Filed: Aug. 24, 2018

(86) PCT No.: PCT/EP2018/072865
§ 371 (c)(1),
(2) Date: Feb. 27, 2020

(87) PCT Pub. No.: WO2019/042881
PCT Pub. Date: Mar. 7, 2019

(65) Prior Publication Data
US 2020/0375207 A1    Dec. 3, 2020

(30) Foreign Application Priority Data

Aug. 28, 2017  (EP) .................................... 17188105

(51) Int. Cl.
| | | |
|---|---|---|
| *A23C 19/068* | (2006.01) | |
| *A23C 19/032* | (2006.01) | |
| *A23C 19/072* | (2006.01) | |
| *A23C 19/076* | (2006.01) | |
| *C12N 1/20* | (2006.01) | |

(52) U.S. Cl.
CPC ...... *A23C 19/0684* (2013.01); *A23C 19/0323* (2013.01); *A23C 19/072* (2013.01); *A23C 19/076* (2013.01); *C12N 1/20* (2013.01); *A23Y 2240/75* (2013.01)

(58) Field of Classification Search
CPC . C12N 1/205; C12R 2001/46; A23Y 2240/75; A23C 19/0684; A23C 19/0323; A23C 19/072; A23C 19/076
See application file for complete search history.

(56) References Cited

U.S. PATENT DOCUMENTS

| | | | |
|---|---|---|---|
| 8,865,238 B2 | 10/2014 | Janzen et al. | |
| 9,060,524 B2 | 6/2015 | Janzen et al. | |
| 9,416,351 B2 | 8/2016 | Janzen et al. | |
| 9,562,221 B2 | 2/2017 | Janzen et al. | |
| 2012/0164275 A1 | 6/2012 | Janzen et al. | |
| 2012/0301575 A1 | 11/2012 | Janzen et al. | |
| 2015/0086675 A1 | 3/2015 | Johansen et al. | |
| 2015/0099273 A1 | 4/2015 | Janzen et al. | |
| 2015/0322415 A1 | 11/2015 | Janzen et al. | |
| 2016/0227803 A1 | 8/2016 | Janzen et al. | |
| 2017/0096635 A1 | 4/2017 | Janzen et al. | |
| 2017/0298457 A1 | 10/2017 | Janzen et al. | |
| 2019/0183160 A1 | 6/2019 | Gilleladen et al. | |
| 2020/0093149 A1 | 3/2020 | Johansen et al. | |
| 2021/0259266 A1* | 8/2021 | Janzen .................. | C12N 1/205 |

FOREIGN PATENT DOCUMENTS

| | | |
|---|---|---|
| WO | WO-2011/026863 A1 | 3/2011 |
| WO | WO-2011/092300 A1 | 8/2011 |
| WO | WO-2013/160413 A1 | 10/2013 |
| WO | WO-2015/193449 A1 | 12/2015 |
| WO | WO-2017/103051 A1 | 6/2017 |
| WO | WO-2017/194650 A | 11/2017 |

OTHER PUBLICATIONS

Anbukkarasi et al., "Production of low browning Mozzarella cheese: Screening and characterization of wild galactose fermenting *Streptococcus thermophilus* strains", International Journal of advanced research, 2013, vol. 1, No. 5, pp. 83-96 (Published online Jul. 2013).
Cui et al., "New Insights into Various Production Characteristics of *Streptococcus thermophilus* Strains", Int. J. Mol. Sci., vol. 17 (Oct. 2016).
De Vin et al., "Molecular and biochemical analysis of the galactose phenotype of dairy *Streptococcus thermophilus* strains reveals four different fermentation profiles", Applied and Environmental Microbiology, vol. 71, No. 7, (Jul. 2005) pp. 3659-3667.
Derkx et al., "The art of strain improvement of industrial lactic acid bacteria without the use of recombinant DNA technology", Microbial Cell Factories, 2014, 13(Suppl 1):S5, pp. 1-13.
Hassan et al., "Factors affecting capsule size and production by lactic acid bacteria used as dairy starter cultures," International Journal of Food Microbiology 64 (2001) 199-203.
Mukherjee et al., "Isolation of Galactose-Fermenting Thermophilic Cultures and Their Use in the Manufacture of Low Browning Mozzarella Cheese", Journal of Dairy Science, vol. 77, No. 10, pp. 2839-2849,1994.
Thomas et al., "Selection of Galactose-Fermenting *Streptococcus thermophilus* in Lactose-Limited Chemostat Cultures", Applied and environmental microbiology, (Jul. 1984) pp. 186-191.
Vaughan et al., "Activation of Silent gal Genes in the lac-gal Regulon of *Streptococcus thermophilus*", Journal of Bacteriology, (Feb. 2001) pp. 1184-1194.
Non-Final Office Action issued in U.S. Appl. No. 17/253,851, dated Mar. 14, 2023 (8 pages).

* cited by examiner

*Primary Examiner* — Changqing Li
(74) *Attorney, Agent, or Firm* — Foley & Lardner LLP

(57) ABSTRACT

Deposited *Streptococcus thermophilus* (ST) strains that e.g. are suitable to be used in an improved method for the manufacture of low browning mozzarella cheese.

11 Claims, No Drawings

STREPTOCOCCUS THERMOPHILUS (ST) CELL TO MAKE E.G. MOZZARELLA CHEESE

CROSS-REFERENCE TO RELATED APPLICATIONS

This application is the U.S. national stage of PCT/EP2018/072865, filed Aug. 24, 2018, and claims priority to European application 17188105.5, filed Aug. 28, 2017.

FIELD OF THE INVENTION

The present invention relates to deposited *Streptococcus thermophilus* (ST) strains that e.g. are suitable to be used in an improved method for the manufacture of low browning mozzarella cheese.

BACKGROUND ART

The food industry uses numerous bacteria, in particular lactic bacteria, in order to improve e.g. the taste and the texture of foods. In the case of the dairy industry, lactic acid bacteria are used intensively in order to bring about the acidification of milk (by fermentation) but also in order to e.g. texturize the product into which they are incorporated.

Starter culture composition/mixture to make mozzarella cheese generally comprises the lactic acid bacterium (LAB) *Streptococcus thermophilus* (ST)—it may sometimes also comprise e.g. relevant *Lactobacillus* strains.

A relatively high concentration of galactose can result in "browning" during heating of cheeses as it is often described when e.g. mozzarella cheese is produced by *S. thermophilus* (ST) for e.g. pizza production.

The browning phenomenon is believed to be due to the Maillard reaction where galactose as reducing sugar is reacting with amino acids/peptides.

Beside this major problem during pizza cheese production, excess amounts of free galactose can also lead to post acidification problems and imbalance in the flora of other dairy product, such as e.g. soft cheeses.

The article of Mukherjee et al. (1994, J Dairy Sci 77:2839-2849) describes the use of so-called galactose non-releasing *Streptococcus* as starter cultures in the manufacture of low browning mozzarella cheese.

The article of Hassan et al. (International Journal of Food Microbiology 64 (2001) 199-203) describes that the ability of some strains of *S. thermophilus* (ST) to use galactose in capsule production could reduce browning of mozzarella cheese during baking by removing a source of reducing sugar.

WO2011/026863A1 (Chr. Hansen) and WO2011/092300A1 (Chr. Hansen) describe that *S. thermophilus* (ST) strains with mutations in the GalK (galactokinase) gene generate a higher viscosity in fermented milk. None of these two WO publications describe above discussed browning of mozzarella cheese related problem.

WO2013/160413A1 (Chr. Hansen) describes herein discussed *Streptococcus thermophilus* (ST) CHCC14994 strain, which was deposited on 3 Apr. 2012 under the accession No. DSM 25838. The CHCC14994 strain is described as a so-called "mother strain" suitable to be used as a starting strain for being mutated in order to obtain novel mutated strains with "mutation in the DNA sequence of the glcK gene". Accordingly, the CHCC14994/DSM25838 strain is not disclosed to be present/comprised in a starter culture composition nor to be used in the manufacturing of a food or feed product of interest (e.g. a dairy product).

SUMMARY OF THE INVENTION

The problem to be solved by the present invention is to provide novel deposited *Streptococcus thermophilus* (ST) strains that e.g. are suitable to be used in an improved method for the manufacture of low browning mozzarella cheese.

The solution relates to herein discussed novel deposited *Streptococcus thermophilus* (ST) strains.

As shown in working examples herein—the herein discussed deposited ST strains are capable of extraordinary reducing the release of galactose also in the presence of high amounts of lactose (as in milk).

As discussed above, the prior art describes use of so-called galactose non-releasing *Streptococcus* as starter cultures in the manufacture of low browning mozzarella cheese.

Accordingly, since the herein deposited strains are capable of providing an extraordinary reduction of the release of galactose they may e.g. be used in an improved method for the manufacture of low browning mozzarella cheese.

As understood by the skilled person in the present context—the herein deposited strains may also be used for making other milk based (e.g. cow milk based) food product, such as e.g. soft cheeses or cheddar.

The herein deposited strains are mutants of relevant parent/mother strains made in the laboratory of the present inventors—i.e. they are novel not "natural" strains comprising novel not earlier described mutations in their respective relevant DNA sequences.

In short, the herein deposited mutant strains were obtained after several mutagenesis/selection rounds, where e.g. the selections were performed via novel combinations of relevant selection criteria—said in other words, the deposited strains were not obtained by what may be termed standard prior art routine mutagenesis/selection work (see e.g. working example herein).

As can be seen in Table 1 of Example 1, by use of the in this Example described special method for isolation of galactose hyper-fermenting mutants from *S. thermophilus* it was possible to obtain ST bacteria able to reduce by around 50% (see e.g. CHCC27912 and CHCC29526) the amounts of excreted galactose in milk as compared to reference ST CHCC4323 bacteria.

ST bacteria able to reduce by at least 20% the amounts of excreted galactose in milk as compared to reference ST CHCC4323 bacteria may herein be termed ST Gal(++) bacteria.

Without being limited to theory—the in Example 1 described special method for isolation of galactose hyper-fermenting ST Gal(++) mutants from *S. thermophilus* may be considered special due to the fact that the galactose reduction level is dramatically increased compared to a herein termed Gal(+) strain. As described in Example 1, the galactose reduction level for CHCC14993, a Gal(+) mutant of CHCC4323, is 17%, whereas the galactose reduction level of CHCC14994, a Gal(++) mutant of CHCC4323, is 30%, compared to the wild type CHCC4323. The galactose reduction level of CHCC29526, a Gal(++) mutant from CHCC4459, is even 52% compared to the reference CHCC4323.

By using the newly developed, not previously described method of sub-culturing in M17-gal broth it was therefore possible to isolate galactose hyper-fermenting mutants with a unique galactose reducing ability.

As discussed below—in working examples were the herein deposited strains of the invention compared to following so-called reference strains:

ST strain CHCC4323: It has what may be termed a GalK natural wildtype sequence (herein termed GalK(−)) and may be seen as a ST reference strain that corresponds to a today commercially relevant used ST strain for making mozzarella cheese;

ST strain 4323-2 (CHCC14993): It comprises a mutation in the GalK (galactokinase) gene (herein termed Gal (+)) and may be seen as a reference strain that corresponds to a strain made according to the description of above discussed WO2011/026863A1 (Chr. Hansen) and WO2011/092300A1 (Chr. Hansen).

It is believed that above discussed reference strains may be seen as reference strains that correspond to herein relevant described strains of the prior art (see e.g. prior art discussion above).

As discussed below—working examples herein show that the herein discussed deposited strains of the invention are capable of reducing the release of galactose also in the presence of high amounts of lactose (as in milk) to a degree, which is extraordinary improved as compared to above discussed reference strains.

Accordingly, a first aspect of the invention relates to a *Streptococcus thermophilus* (ST) cell, wherein the cell is at least one cell selected from the group consisting of:

(a) a *Streptococcus thermophilus* cell CHCC19097 deposited with registration number DSM 32594;
(b) a *Streptococcus thermophilus* cell CHCC19100 deposited with registration number DSM 32595;
(c) a *Streptococcus thermophilus* cell CHCC27912 deposited with registration number DSM 32596;
(d) a *Streptococcus thermophilus* cell CHCC29526 deposited with registration number DSM 32597;
(e) a *Streptococcus thermophilus* cell CHCC29530 deposited with registration number DSM 32598;
(f) a *Streptococcus thermophilus* cell CHCC29525 deposited with registration number DSM 32897;
(g) a *Streptococcus thermophilus* cell CHCC30963 deposited with registration number DSM 32898; and
(h) a *Streptococcus thermophilus* cell CHCC30964 deposited with registration number DSM 32900.

It is clear for the skilled person that by using the herein discussed deposited strains as starting material, the skilled person can routinely, by conventional mutagenesis or reisolation techniques, obtain further mutants or derivatives thereof that retain the herein described relevant features and advantages. Accordingly, the term "a mutant thereof" or "a mutant of a deposited strain" relates to a mutant strain obtained by using the deposited strain as starting material.

As discussed above, WO2013/160413A1 (Chr. Hansen) describes herein discussed *Streptococcus thermophilus* (ST) CHCC14994 strain, which was deposited on 3 Apr. 2012 under the accession No. DSM 25838. The CHCC14994/DSM25838 strain is not disclosed to be present/comprised in a starter culture composition nor to be used in the manufacturing a food or feed product of interest (e.g. a dairy product).

Accordingly, a second aspect of the invention relates to a method to obtain a mutant strain of a deposited cell of the first aspect or the *Streptococcus thermophilus* cell CHCC14994 deposited with registration number DSM 25838 comprising using at least one of the deposited strains of the first aspect or DSM 25838 as starting strain, making mutants of the deposited strain and isolating a novel mutant strain, wherein the mutant strain has retained the property of being capable of reducing the release of galactose in the presence of lactose of the deposited strain.

The property of the obtained mutant strain relating to "being capable of reducing the release of galactose in the presence of lactose" may be measured as described in working example herein—based on the description herein, this is routine work for the skilled person.

It is evident, that a mutant strain obtained according to the method of the second aspect may be used to e.g. a method of manufacturing a food or feed product as discussed herein (e.g. a method of the fourth aspect as discussed herein).

A third aspect of the invention relates to a starter culture composition comprising at least one of the *Streptococcus thermophilus* (ST) cells of the first aspect or the *Streptococcus thermophilus* cell CHCC14994 deposited with registration number DSM 25838, wherein the starter culture composition is having a concentration of viable cells of the first aspect or DSM 25838, which is in the range of $10^4$ to $10^{14}$ cfu per gram of the composition.

As understood, the composition of the third aspect may e.g. comprise $10^8$ cfu per gram of e.g. only one of the herein described deposited strains or it may e.g. comprise $10^8$ cfu per gram of one deposited strain plus $10^8$ cfu per gram of another of the deposited strains, which would give a composition with $2\times10^8$ cfu per gram of viable cells of the first aspect.

Further, the composition may comprise other cells such as e.g. *Lactobacillus* and/or *Lactococcus* cells.

A fourth aspect of the invention relates to a method of manufacturing a food or feed product comprising adding a starter culture composition according to the third aspect to a food or feed product starting material and keeping the thus inoculated starting material under conditions where the *Streptococcus thermophilus* (ST) cells are metabolically active.

Embodiment of the present invention is described below, by way of examples only.

DETAILED DESCRIPTION OF THE INVENTION

Deposited Strains/Cells

A sample of the *Streptococcus thermophilus* cell CHCC14994 has been deposited at DSMZ (Deutsche Sammlung von Mikroorganismen und Zellkulturen GmbH, Inhoffenstr. 7B, D-38124 Braunschweig) under the accession number DSM 25838 with a deposit date of 3 Apr. 2012. The deposit has been made under the conditions of the Budapest Treaty on the International Recognition of the Deposit of Microorganisms for the Purposes of Patent Procedure.

As discussed above, this deposited strain is described in WO2013/160413A1 (Chr. Hansen).

A sample of the novel *Streptococcus thermophilus* cell CHCC19097 has been deposited at DSMZ (Deutsche Sammlung von Mikroorganismen und Zellkulturen GmbH, Inhoffenstr. 7B, D-38124 Braunschweig) under the accession number DSM 32594 with a deposit date of 22 Aug. 2017. The deposit has been made under the conditions of the Budapest Treaty on the International Recognition of the Deposit of Microorganisms for the Purposes of Patent Procedure.

A sample of the novel *Streptococcus thermophilus* cell CHCC19100 has been deposited at DSMZ (Deutsche Sammlung von Mikroorganismen und Zellkulturen GmbH, Inhoffenstr. 7B, D-38124 Braunschweig) under the accession number DSM 32595 with a deposit date of 22 Aug. 2017. The deposit has been made under the conditions of the Budapest Treaty on the International Recognition of the Deposit of Microorganisms for the Purposes of Patent Procedure.

A sample of the novel *Streptococcus thermophilus* cell CHCC27912 has been deposited at DSMZ (Deutsche Sammlung von Mikroorganismen und Zellkulturen GmbH, Inhoffenstr. 7B, D-38124 Braunschweig) under the accession number DSM 32596 with a deposit date of 22 Aug. 2017. The deposit has been made under the conditions of the Budapest Treaty on the International Recognition of the Deposit of Microorganisms for the Purposes of Patent Procedure.

A sample of the novel *Streptococcus thermophilus* cell CHCC29526 has been deposited at DSMZ (Deutsche Sammlung von Mikroorganismen und Zellkulturen GmbH, Inhoffenstr. 7B, D-38124 Braunschweig) under the accession number DSM 32597 with a deposit date of 22 Aug. 2017. The deposit has been made under the conditions of the Budapest Treaty on the International Recognition of the Deposit of Microorganisms for the Purposes of Patent Procedure.

A sample of the novel *Streptococcus thermophilus* cell CHCC29530 has been deposited at DSMZ (Deutsche Sammlung von Mikroorganismen und Zellkulturen GmbH, Inhoffenstr. 7B, D-38124 Braunschweig) under the accession number DSM 32598 with a deposit date of 22 Aug. 2017. The deposit has been made under the conditions of the Budapest Treaty on the International Recognition of the Deposit of Microorganisms for the Purposes of Patent Procedure.

A sample of the novel *Streptococcus thermophilus* cell CHCC29525 has been deposited at DSMZ (Deutsche Sammlung von Mikroorganismen und Zellkulturen GmbH, Inhoffenstr. 7B, D-38124 Braunschweig) under the accession number DSM 32897 with a deposit date of 16 Aug. 2018. The deposit has been made under the conditions of the Budapest Treaty on the International Recognition of the Deposit of Microorganisms for the Purposes of Patent Procedure.

A sample of the novel *Streptococcus thermophilus* cell CHCC30963 has been deposited at DSMZ (Deutsche Sammlung von Mikroorganismen und Zellkulturen GmbH, Inhoffenstr. 7B, D-38124 Braunschweig) under the accession number DSM 32898 with a deposit date of 16 Aug. 2018. The deposit has been made under the conditions of the Budapest Treaty on the International Recognition of the Deposit of Microorganisms for the Purposes of Patent Procedure.

A sample of the novel *Streptococcus thermophilus* cell CHCC30964 has been deposited at DSMZ (Deutsche Sammlung von Mikroorganismen and Zellkulturen GmbH, Inhoffenstr. 7B, D-38124 Braunschweig) under the accession number DSM 32900 with a deposit date of 16 Aug. 2018. The deposit has been made under the conditions of the Budapest Treaty on the International Recognition of the Deposit of Microorganisms for the Purposes of Patent Procedure.

A Starter Culture Comprising a ST Cell as Described Herein

The ST cell as described herein is useful as starter culture in the production of food or feed products.

Typically, such a starter culture composition comprises the bacteria in a concentrated form including frozen, dried or freeze-dried concentrates typically having a concentration of viable cells, which is in the range of $10^4$ to $10^{14}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g.

The composition may as further components contain cryoprotectants and/or conventional additives including nutrients such as yeast extracts, sugars and/or vitamins.

As it is normal in the production of lactic acid bacterial fermentation processes to apply mixed cultures of lactic acid bacteria, the composition will in certain embodiments comprise a multiplicity of strains either belonging to the same species or belonging to different species.

For instance, it may be preferred that the composition also comprises other cells such as e.g. *Lactobacillus* cells and/or *Lactococcus* cells.

A Method of Manufacturing a Food or Feed Product

As said above, an aspect of the invention relates to a method of manufacturing a food or feed product comprising adding a starter culture composition as described herein to a food or feed product starting material and keeping the thus inoculated starting material under conditions where the ST cells are metabolically active.

Useful food product starting materials include any material which is conventionally subjected to a lactic acid bacterial fermentation step such as milk (e.g. soy milk or cow milk, preferably cow milk), vegetable materials, meat products, fruit juices, must, doughs and batters.

The fermented products, which are obtained by the method, include as typical examples dairy products such as fermented milk, yogurt, cheese including fresh cheese products, soft cheese products, cheddar, mozzarella or buttermilk.

In a preferred embodiment, the dairy product is soft cheese, cheddar cheese, pasta filata cheese or mozzarella cheese—more preferably, the dairy product is pasta filata cheese, cheddar cheese or mozzarella cheese—most preferably the dairy product is mozzarella cheese or cheddar cheese (preferably used for making pizza).

In further embodiments, the substrate material is a starting material for an animal feed such as silage, e.g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

EXAMPLES

Example 1: Deposited *Streptococcus thermophilus* (ST) Strains—Capable of Extraordinary Reducing the Release of Galactose Also in the Presence of High Amounts of Lactose (as in Milk)

Reference Strains:
ST strain CHCC4323: It has what may be termed a GalK natural wildtype sequence (herein termed GalK(−)) and may be seen as a ST reference strain that corresponds to a today commercially relevant used ST strains for making mozzarella cheese;
ST strain 4323-2 (CHCC14993): It comprises a mutation in the GalK (galactokinase) gene (herein termed Gal (+)) and may be seen as a reference strain that corresponds to a strain made according to the description of above discussed WO2011/026863A1 (Chr. Hansen) and WO2011/092300A1 (Chr. Hansen).

Deposited Strains of the Present Invention:

CHCC14994: DSM 25838 ST strain—disclosed in WO2013/160413A1 (Chr. Hansen).

CHCC19097: Novel DSM 32594 ST strain as described herein.

CHCC19100: Novel DSM 32595 ST strain as described herein.

CHCC27912: Novel DSM 32596 ST strain as described herein.

CHCC29526: Novel DSM 32597 ST strain as described herein.

CHCC29530: Novel DSM 32598 ST strain as described herein.

Isolation of Galactose Hyper-Fermenting Mutants from S. thermophilus:

Prior to the mutant isolation the strains were streaked on M17 agar plates with 2% galactose (M17-gal plates). The wild type (wt) strains did not grow significantly on galactose as sole carbohydrate source.

Overnight cultures were then plated on M17-gal plates and several colonies could be isolated after two days of growth at 37° C. Several mutants were purified on M17-gal plates and retested in M17 broth containing 2% galactose as sole carbohydrate. From purified galactose positive mutants second generation galactose hyperfermenting mutants were isolated by sub-culturing in M17-gal broth with daily 1% reinoculation from the fully outgrown overnight culture; incubation occurred at 37° C. After dilution plating, 100 single colonies were isolated from M17-gal plates and inoculated in microtitre plates with M17-gal broth. The OD was followed by an OD-reader and the clones showing a better increase of OD during 16 hours of incubation at 37° C. as the wt strain were further purified and characterized.

The wt S. thermophilus strains from which galactose-hyperfermenting mutants were isolated are:
CHCC9861
CHCC4459
CHCC4426
CHCC4323
CHCC7018
CHCC3050

The galactose-hyperfermenting mutants showing an unusually high galactose fermenting ability and reduced galactose excretion into the media are (mutant/wt):
CHCC27912/CHCC9861
CHCC29526/CHCC4459
CHCC29530/CHCC4426
CHCC14994/CHCC4323
CHCC19100/CHCC7018
CHCC19097/CHCC3050

The example includes also a typical galactose positive strain, isolated as first generation mutant from CHCC4323, named CHCC14993. CHCC14993 showed a typical galactose reduction in milk of 17% (reduction of galactose excretion in milk compared to wt CHCC4323).

Fermentation of Milk

Mutant strains were inoculated in milk 1% from overnight cultures and incubated for 24 hours at 37° C. The acidification activity of mutants was similar to the wt strain. At the end of fermentation samples were taken to measure galactose content in the fermented milk and with this the reduction of excreted galactose compared to the galactose negative reference strain CHCC4323 and reference strain 4323-2 (CHCC14993).

Results—Analysis of Acidification and Excreted Galactose in the Fermented Milk

All the tested ST strains had similar acidification profiles—i.e. the deposited ST strains of the present invention had not lost their capacity to acidify fast in milk.

The amounts of excreted galactose for the different tested strains are shown in Table 1 below:

Table 1 indicates the amount of galactose in milk and the reduction of galactose compared to the reference CHCC4323. Whereas the typical gal+ mutant CHCC14993 showed a galactose reduction of less than 20%, the hyper-fermenting mutants showed a much higher reduction up to 52%, meaning that the amount of free galactose is much lower when e.g. pizza cheese is produced with the new mutants, which is leading to reduced browning during baking.

TABLE 1

Average of two measurements from carbohydrate analysis. Results are shown in mg/g.

| Strain | Galactose | Galactose reduction (%) |
|---|---|---|
| CHCC4323 | 7.1 | 0 |
| CHCC14993 | 5.9 | 17 |
| CHCC27912 | 3.4 | 52 |
| CHCC29526 | 3.4 | 52 |
| CHCC29530 | 4.9 | 31 |
| CHCC14994 | 5.0 | 30 |
| CHCC19100 | 4.1 | 42 |
| CHCC19097 | 5.1 | 28 |

Conclusions

The results demonstrated that the herein deposited strains of the present invention are capable of reducing the release of galactose also in the presence of high amounts of lactose (as in milk) to a degree, which is extraordinarily improved as compared to above discussed reference strains.

Example 2: Deposited *Streptococcus thermophilus* (ST) Strains—Capable of Extraordinary Reducing the Release of Galactose Also in the Presence of High Amounts of Lactose (as in Milk)

Reference Strains:
Same as Example 1 above.
Deposited Strains of the Present Invention:
CHCC29525: Novel DSM 32897 strain as described herein.
CHCC30963: Novel DSM 32898 strain as described herein.
CHCC30964: Novel DSM 32900 strain as described herein.

Isolation of Galactose Hyper-Fermenting Mutants from S. thermophilus:

Prior to the mutant isolation the strains were streaked on M17 agar plates with 2% galactose (M17-gal plates). The wild type (wt) strains did not grow significantly on galactose as sole carbohydrate source.

Overnight cultures were then plated on M17-gal plates and several colonies could be isolated after two days of growth at 37° C. Several mutants were purified on M17-gal plates and retested in M17 broth containing 2% galactose as sole carbohydrate.

From purified galactose positive mutants second generation galactose hyperfermenting mutants were isolated by sub-culturing in M17-gal broth with daily 1% reinoculation from the fully outgrown overnight culture; incubation occurred at 37° C. After dilution plating, 100 single colonies were isolated from M17-gal plates and inoculated in microtitre plates with M17-gal broth. The OD was followed by an OD-reader and the clones showing a better increase of OD during 16 hours of incubation at 37° C. as the wt strain were further purified and characterized.

The wt *S. thermophilus* strains from which galactose-hyperfermenting mutants were isolated are:
CHCC4458
CHCC4459

The galactose-hyperfermenting mutants showing an unusually high galactose fermenting ability and reduced galactose excretion into the media are (mutant/wt):
CHCC30963/CHCC4458
CHCC30964/CHCC4458
CHCC29525/CHCC4459

The example includes also a typical galactose positive strain, isolated as first generation mutant from CHCC4323, named CHCC14993. CHCC14993 showed a typical galactose reduction in milk of 17% (reduction of galactose excretion in milk compared to wt CHCC4323).

Fermentation of Milk
Same as Example 1 above.
Results—Analysis of Acidification and Excreted Galactose in the Fermented Milk All the tested ST strains had similar acidification profiles—i.e. the deposited ST strains of the present invention had not lost their capacity to acidify fast in milk.

The amounts of excreted galactose for the different tested strains are shown in Table 2 below:

Table 2 indicates the amount of galactose in milk and the reduction of galactose compared to the reference CHCC4323. Whereas the typical gal+ mutant CHCC14993 showed a galactose reduction of less than 20%, the hyperfermenting mutants showed a much higher reduction up to 57%, meaning that the amount of free galactose is much lower when e.g. pizza cheese is produced with the new mutants, which is leading to reduced browning during baking.

TABLE 2

Average of two measurements from carbohydrate analysis. Results are shown in mg/g.

| Strain | Galactose | Galactose reduction (%) |
|---|---|---|
| CHCC4323 | 7.0 | 0 |
| CHCC14993 | 5.9 | 16 |
| CHCC29525 | 3.0 | 57 |
| CHCC30963 | 3.7 | 47 |
| CHCC30964 | 4.8 | 31 |

Conclusions

The results demonstrated that the herein deposited strains of the present invention are capable of reducing the release of galactose also in the presence of high amounts of lactose (as in milk) to a degree, which is extraordinarily improved as compared to above discussed reference strains.

REFERENCES

1. Mukherjee et al (1994, J Dairy Sci 77:2839-2849)
2. Hassan et al. (International Journal of Food Microbiology 64 (2001) 199-203)
3. WO2011/026863A1 (Chr. Hansen)
4. WO2011/092300A1 (Chr. Hansen)
5. WO2013/160413A1 (Chr. Hansen)

The invention claimed is:

1. A mutant *Streptococcus thermophilus* (ST) cell selected from:
   (a) a cell of *Streptococcus thermophilus* strain CHCC19097 deposited with Deutsche Sammlung von Mikroorganismen and Zellkulturen GmbH (DSMZ) under accession number DSM 32594;
   (b) a cell of *Streptococcus thermophilus* strain CHCC19100 deposited with DSMZ under accession number DSM 32595;
   (c) a cell of *Streptococcus thermophilus* strain CHCC27912 deposited with DSMZ under accession number DSM 32596;
   (d) a cell of *Streptococcus thermophilus* strain CHCC29526 deposited with DSMZ under accession number DSM 32597;
   (e) a cell of *Streptococcus thermophilus* strain CHCC29530 deposited with DSMZ under accession number DSM 32598;
   (f) a cell of *Streptococcus thermophilus* strain CHCC29525 deposited with DSMZ under accession number DSM 32897;
   (g) a cell of *Streptococcus thermophilus* strain CHCC30963 deposited with DSMZ under accession number DSM 32898; and
   (h) a cell of *Streptococcus thermophilus* strain CHCC30964 deposited with DSMZ under accession number DSM 32900.

2. A method for obtaining a mutant *Streptococcus thermophilus* (ST) strain, comprising mutating a cell selected from a mutant cell of claim 1 as a starting cell, and isolating a further mutant that has retained capability of reducing release of galactose in the presence of lactose as compared to the starting cell.

3. A starter culture composition comprising viable cells of one or more mutant *Streptococcus thermophilus* (ST) strains of claim 1.

4. The starter culture composition of claim 3, wherein the concentration of viable cells of the one or more mutant *Streptococcus thermophilus* strains is in the range of $10^7$ to $10^{14}$ colony forming units (CFU) per gram of the composition.

5. The starter culture composition of claim 3, further comprising a cell of *Streptococcus thermophilus* strain CHCC14994 deposited with DSMZ under accession number DSM 25838 in a concentration in the range of $10^4$ to $10^{14}$ CFU per gram of the composition.

6. A method of manufacturing a food or feed product comprising adding a starter culture composition according to claim 3 to a food or feed product starting material to obtain inoculated food or feed product material, and maintaining the inoculated food or feed product material under conditions where the *Streptococcus thermophilus* (ST) cells are metabolically active.

7. The method of claim 6, wherein the product is a food product.

8. The method of claim 7, wherein the food product is dairy product.

9. The method of claim 8, wherein the dairy product is fermented milk, yogurt, buttermilk, fresh cheese, soft cheese, cheddar cheese, mozzarella cheese, or pasta filata cheese.

10. The method of claim 9, wherein the dairy product is soft cheese, cheddar cheese, pasta filata cheese or mozzarella cheese.

11. The method of claim 10, wherein the dairy product is mozzarella cheese or cheddar cheese.

\* \* \* \* \*

UNITED STATES PATENT AND TRADEMARK OFFICE
CERTIFICATE OF CORRECTION

PATENT NO. : 11,690,384 B2
APPLICATION NO. : 16/642787
DATED : July 4, 2023
INVENTOR(S) : Thomas Janzen and Ditte Ellegaard Christiansen Page 1 of 1

It is certified that error appears in the above-identified patent and that said Letters Patent is hereby corrected as shown below:

On the Title Page

Item (54) (Title) and in the Specification, Column 1, Line 1:
Change "THERMOPHTLUS" to --THERMOPHILUS--.

Signed and Sealed this
Fifteenth Day of August, 2023

Katherine Kelly Vidal
*Director of the United States Patent and Trademark Office*